United States Patent
Sherwin (10) Patent No.: US 9,521,943 B2
(45) Date of Patent: Dec. 20, 2016

(54) LENS PROTECTOR FOR ENDOSCOPIC DEVICES

(75) Inventor: Daniel Sherwin, Jerusalem (IL)

(73) Assignee: Cleanoscope Inc., Antwerpen (BE)

( * ) Notice: Subject to any disclaimer, the term of this patent is extended or adjusted under 35 U.S.C. 154(b) by 511 days.

(21) Appl. No.: 13/639,693

(22) PCT Filed: Apr. 11, 2011

(86) PCT No.: PCT/IL2011/000297
§ 371 (c)(1),
(2), (4) Date: Apr. 18, 2013

(87) PCT Pub. No.: WO2011/128894
PCT Pub. Date: Oct. 20, 2011

(65) Prior Publication Data
US 2013/0197311 A1 Aug. 1, 2013

(30) Foreign Application Priority Data

Apr. 12, 2010 (IL) .......................... 205022

(51) Int. Cl.
*A61B 1/04* (2006.01)
*A61B 1/06* (2006.01)
(Continued)

(52) U.S. Cl.
CPC ....... *A61B 1/00096* (2013.01); *A61B 1/00101* (2013.01); *A61B 1/06* (2013.01); *A61B 1/125* (2013.01)

(58) Field of Classification Search
CPC . A61B 1/00165; A61B 1/00096; A61B 1/126; A61B 1/00101; A61B 1/00103; A61B 1/00112; A61B 1/00163; A61B 1/053; A61B 1/06; A61B 1/125; G02B 21/0028; G02B 23/24; G02B 23/2423
(Continued)

(56) References Cited

U.S. PATENT DOCUMENTS 4,275,343 A 6/1981 Fulton et al.
4,558,691 A * 12/1985 Okada ........................... 600/117
(Continued)

FOREIGN PATENT DOCUMENTS

AU 199515074 10/1996
DE 10 2008 031881 B3 6/2009
(Continued)

OTHER PUBLICATIONS

Extended European Search Report from corresponding European Application No. 11 768 558.6 dated May 19, 2014 (7 pgs).
(Continued)

*Primary Examiner* — John P Leubecker
*Assistant Examiner* — Arnaldo Torres Diaz
(74) *Attorney, Agent, or Firm* — Alston & Bird LLP (57) ABSTRACT

The invention is an endoscopic device comprising a proximal end, a distal end, and a first location positioned between the proximal end and the distal end. The endoscopic device comprises an optical system that terminates with an objective lens that is located at the first position. A lens protector unit is positioned between the objective lens and the distal tip in order to protect the objective lens. The lens protector unit comprises a rotating window that is located at the distal end of the endoscopic device. The endoscopic device also comprises a source of light located on the distal end. The source of light is adapted to illuminate the space in front of the distal end of the endoscopic device.

15 Claims, 6 Drawing Sheets

(51) Int. Cl.
*A61B 1/00* (2006.01)
*A61B 1/12* (2006.01)

(58) Field of Classification Search
USPC ....... 600/176, 157, 169, 121, 175, 129, 172; 396/448, 544; 348/75
See application file for complete search history.

(56) References Cited

U.S. PATENT DOCUMENTS

| | | | | |
|---|---|---|---|---|
| 4,660,982 A * | 4/1987 | Okada | ............ | 356/636 |
| 4,706,653 A * | 11/1987 | Yamamoto | ............ | 600/175 |
| 4,747,661 A * | 5/1988 | Ohkuwa | ............ | 385/118 |
| 4,787,370 A * | 11/1988 | Kanamori | ............ | 600/175 |
| 4,802,460 A * | 2/1989 | Ohkuwa et al. | ............ | 600/177 |
| 4,856,495 A * | 8/1989 | Tohjoh et al. | ............ | 600/175 |
| 4,860,732 A * | 8/1989 | Hasegawa et al. | ............ | 600/109 |
| 4,941,457 A * | 7/1990 | Hasegawa | ............ | 600/142 |
| 5,051,824 A * | 9/1991 | Nishigaki | ............ | 348/68 |
| 5,223,880 A | 6/1993 | Rapp | | |
| 5,301,061 A * | 4/1994 | Nakada et al. | ............ | 359/362 |
| 5,315,333 A | 5/1994 | Nash | | |
| 5,377,669 A * | 1/1995 | Schulz | ............ | 600/121 |
| 5,447,148 A * | 9/1995 | Oneda et al. | ............ | 600/131 |
| 5,518,501 A * | 5/1996 | Oneda et al. | ............ | 600/127 |
| 5,547,457 A * | 8/1996 | Tsuyuki et al. | ............ | 600/175 |
| 5,584,793 A * | 12/1996 | Sauer et al. | ............ | 600/121 |
| 5,605,532 A * | 2/1997 | Schermerhorn | ............ | 600/169 |
| 5,647,840 A * | 7/1997 | D'Amelio et al. | ............ | 600/169 |
| 5,743,846 A * | 4/1998 | Takahashi et al. | ............ | 600/166 |
| 5,779,625 A | 7/1998 | Suzuki et al. | | |
| 5,817,015 A * | 10/1998 | Adair | ............ | 600/121 |
| 5,916,148 A * | 6/1999 | Tsuyuki | ............ | 600/176 |
| 5,966,168 A * | 10/1999 | Miyazaki | ............ | 348/68 |
| 5,989,185 A * | 11/1999 | Miyazaki | ............ | 600/175 |
| 6,095,970 A * | 8/2000 | Hidaka et al. | ............ | 600/110 |
| 6,142,932 A * | 11/2000 | Morizumi | ............ | 600/166 |
| 6,184,923 B1 * | 2/2001 | Miyazaki | ............ | 348/75 |
| 6,206,825 B1 * | 3/2001 | Tsuyuki | ............ | 600/182 |
| 6,503,196 B1 * | 1/2003 | Kehr et al. | ............ | 600/176 |
| 6,976,956 B2 * | 12/2005 | Takahashi et al. | ............ | 600/166 |
| 7,033,317 B2 * | 4/2006 | Pruitt | ............ | 600/133 |
| 7,104,657 B2 | 9/2006 | Sherwin | | |
| 7,435,218 B2 * | 10/2008 | Krattiger et al. | ............ | 600/175 |
| 7,455,637 B2 * | 11/2008 | Takahashi | ............ | 600/169 |
| 7,871,373 B2 * | 1/2011 | Yamada | ............ | 600/175 |
| 8,182,421 B2 | 5/2012 | Muckner et al. | | |
| 8,182,422 B2 * | 5/2012 | Bayer et al. | ............ | 600/175 |
| 8,259,167 B2 * | 9/2012 | Ishiwata et al. | ............ | 348/65 |
| 8,920,311 B2 * | 12/2014 | LaBombard | ............ | 600/127 |
| 2002/0082476 A1 * | 6/2002 | Takahashi et al. | ............ | 600/173 |
| 2002/0161278 A1 * | 10/2002 | Nakamura | ............ | 600/111 |
| 2003/0092982 A1 * | 5/2003 | Eppstein | ............ | A61B 1/313 600/411 |
| 2003/0137752 A1 * | 7/2003 | Sherwin | ............ | 359/809 |
| 2004/0143162 A1 * | 7/2004 | Krattiger et al. | ............ | 600/175 |
| 2005/0131280 A1 * | 6/2005 | Rovegno | ............ | 600/176 |
| 2005/0240077 A1 * | 10/2005 | Rovegno | ............ | 600/108 |
| 2007/0073108 A1 * | 3/2007 | Takahashi | ............ | 600/169 |
| 2007/0149856 A1 * | 6/2007 | Segawa | ............ | 600/169 |
| 2008/0045800 A2 * | 2/2008 | Farr | ............ | 600/179 |
| 2008/0081948 A1 | 4/2008 | Weisenburgh et al. | | |
| 2009/0009595 A1 * | 1/2009 | Ishiwata et al. | ............ | 348/68 |
| 2009/0160935 A1 * | 6/2009 | Rovegno | ............ | 348/65 |
| 2010/0010313 A1 | 1/2010 | Muckner et al. | | |

FOREIGN PATENT DOCUMENTS

| | | |
|---|---|---|
| WO | WO 01/61408 A1 | 8/2001 |
| WO | WO 2008/082928 A1 | 7/2008 |

OTHER PUBLICATIONS

International Preliminary Report on Patentability, Written Opinion, and International Search Report from corresponding International Application No. PCT/IL2011/000297 (7 pgs).

* cited by examiner

LENS PROTECTOR FOR ENDOSCOPIC DEVICES

FIELD OF THE INVENTION

The present invention is related to the field of protection of the objective lens of viewing devices from the environment. Specifically the invention relates to the field of protection of the objective lenses of endoscopic devices by means of centrifugal lens protectors.

BACKGROUND OF THE INVENTION

Various optical systems are required to operate in adverse environments, in which solid particles and/or fluid droplets and/or other agglomerations of one or more materials of various stickiness or viscosity (herein collectively termed "debris") may adhere to the lens and reduce image quality.

A particularly difficult environment to view is the inside of the human body. Various medical instruments have been devised for this purpose. Endoscopes and laparoscopes are devices used for observation, diagnosis, and treatment, e.g. biopsy or cauterization inside a human or animal body. They comprise an objective lens system, normally at the distal end and means for carrying the images gathered to the proximal end of the device where they can be directly viewed or displayed allowing the operator to observe the space in front of the objective lens. The objective lens can be part of a camera, an optical relay system, or can focus the image onto a fiber optic cable that transfers the image to the viewer. Commonly an endoscope lens becomes at least partially occluded by body fluids and particles. In many cases the occlusion becomes so great that the endoscope becomes inoperative. In such circumstance the lens must cleaned. One method of cleaning the lens is to spray the outer surface of the lens with a jet of water, air or other gas. The water or gas is supplied to one or more nozzles on the distal end adjacent the lens through channels that are an integral part of the endoscope assembly. In some instances the endoscope must be withdrawn from the body for cleaning and reinserted—a time-consuming, risk-increasing and often uncomfortable procedure.

Another solution to this problem is a centrifugal lens protector. A centrifugal lens protector comprises a spinning glass disc that is placed in front of the lens, so that the debris is intercepted by the disc. The centrifugal force generated by the disc as it rotates throws the debris towards the circumference of the disc, where it falls off or sometimes accumulates but in any case no longer interferes with the image.

U.S. Pat. No. 5,223,880 to Rapp describes a camera protector in which the disc is integrated with a rotor of a magnetic motor, with a casing surrounding the disc being the motor housing.

U.S. Pat. No. 5,315,333 to Nash provides a single motor coupled to the disc using a band. The disc is mounted on two lines of bearings. The lens protection device is mounted on the camera, to isolate lens from gyroscopic and vibration forces.

Australian application 9515074 describes another band-based system, in which the disc is said to rotate at between 2600 and 3000 RPM. It is suggested to use a curved or hydrophobic surface to assist in water removal. The motor can be powered using the camera battery pack or using a separate battery.

U.S. Pat. No. 7,104,657 by the inventor of the present invention, the description of which, including publications referenced therein, is incorporated herein by reference provides a lens protector for medical viewing devices. The lens protector is comprised of a rotating window and a motor that causes the rotation. Both of these components are enclosed by a casing located at the distal tip of an endoscopic device in front of the objective lens of the viewing system. The casing, motor, and rotating window are supplied as a unit that can be attached in various ways described in the patent to any existing endoscopic device. In practice, it has been discovered that the use of the invention does indeed solve the problem of the accumulation of body fluids and particles in front of the lens but nevertheless the picture quality is sometimes degraded.

Any endoscopic device that is equipped to provide visualization of the treatment region within a body cavity comprises illumination means, e.g. optical fibers or LEDs, located next to the objective lens, in order to illuminate the area of interest. Because the rotating window of the lens protector in U.S. Pat. No. 7,104,657 also covers the illumination means, some of the light emitted from the endoscope is partially reflected from the inside of the window onto the lens. This back reflected light is the cause of the image quality degradation mentioned above.

It is therefore a purpose of the present invention to provide endoscopic devices that are equipped with rotating lens protectors for the objective lens of the visualization means, wherein back reflection of light from the illumination source is prevented.

Further purposes and advantages of this invention will appear as the description proceeds.

SUMMARY OF THE INVENTION

The invention is an endoscopic device comprising a proximal end, a distal end, and a first location positioned between the proximal end and the distal end. The endoscopic device comprises an optical system that terminates with an objective lens that is located at the first position. A lens protector unit is positioned between the objective lens and the distal tip in order to protect the objective lens. The lens protector unit comprises a rotating window that is located at the distal end of the endoscopic device. The endoscopic device also comprises a source of light located on the distal end. The source of light is adapted to illuminate the space in front of the distal end of the endoscopic device.

An embodiment of the invention is an endoscopic device whose distal portion comprises:
  a. an insertion shaft comprising:
    i. a light carrier located adjacent to the outer surface on one side of the interior of the insertion section;
    ii. a central lumen, comprising a portion that projects forward from the end of the light carrier;
    iii. an objective lens fitted to the distal end of the projecting portion of the central lumen; and
  b. a lens protector unit comprising:
    i. a motor assembly;
    ii. a rotatable transparent window attached to the distal end of the motor assembly;
    iii. a housing that encloses the components of the motor assembly;
    iv. a light carrier located adjacent to the outer surface on one side of the interior of the lens protector unit; and
    v. an outer casing that encloses all components of the lens protector unit.

The dimensions and shape of the projecting portion of the central lumen are determined such that the projecting portion can be inserted into the hollow center of the motor assembly until the objective lens is in close proximity to the rotatable transparent window.

In addition the proximal end of the light carrier of the lens protector unit is configured to match the distal end of the light carrier of the insertion shaft, thereby allowing transport of light from the insertion shaft to the distal end of the lens protector unit.

In embodiments of the endoscopic device of the invention the rotatable transparent window is integral with a rotor of a motor of the motor assembly.

In embodiments of the endoscopic device of the invention the housing is integral with a stator of a motor of the motor assembly.

In embodiments of the endoscopic device of the invention a motor of the motor assembly is a magnetic motor.

In embodiments of the endoscopic device of the invention the motor comprises a plurality of axially disposed magnets, attached to the rotatable transparent window.

In embodiments of the endoscopic device of the invention the stator comprises three separate coils each of which is connected via electrical leads to a different phase of a DC power supply. These embodiments of the endoscopic device can comprise an electric circuit adapted to activate the motor using back EMF switching.

Embodiments of the endoscopic device of the invention comprise an electric circuit adapted to supply current to heat the rotatable transparent window. The heating current can be supplied as an AC current to the coils of the stator or as either an AC or a DC current to a separate coil provided for the purpose of heating the rotatable transparent window. The endoscopic device can comprise a temperature sensor near the rotatable transparent window to provide feedback to the circuitry which supplies the heating current in order to supply the current at a rate which maintains the temperature in the vicinity of the rotatable transparent window at a predetermined temperature. In embodiments of the endoscopic device of the invention the predetermined temperature is 37° C.

Embodiments of the endoscopic device of the invention comprise one or more working channels that pass through the endoscopic device from its proximal end to the distal end of the lens protector unit.

In embodiments of the endoscopic device of the invention the insertion shaft is sterilizable. In embodiments of the endoscopic device of the invention the lens protector unit is discarded after a single use.

All the above and other characteristics and advantages of the invention will be further understood through the following illustrative and non-limitative description of embodiments thereof, with reference to the appended drawings. In the drawings the same numerals are sometimes used to indicate the same elements in different drawings.

DETAILED DESCRIPTION OF EMBODIMENTS OF THE INVENTION

Figure 1:
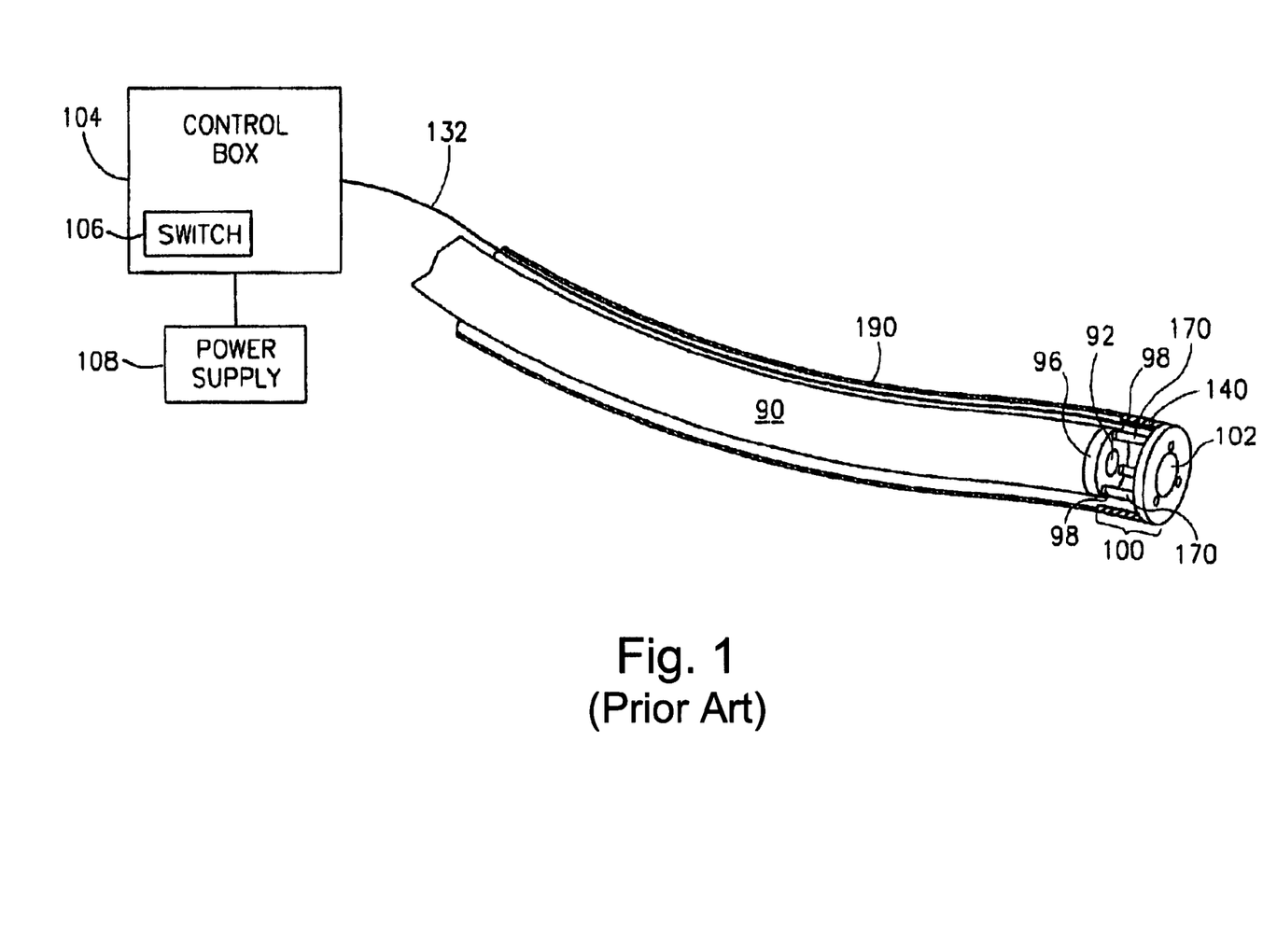
FIG. 1 is a schematic view of a lens protector with a sheath enclosing an endoscope, in accordance with some embodiments of the prior art invention described in U.S. Pat. No. 7,104,657.
Figure 2:
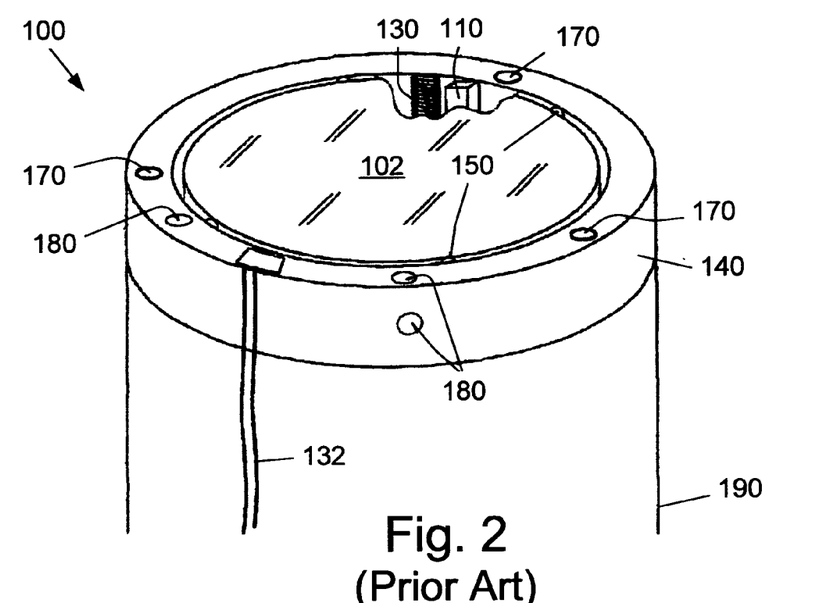
FIG. 2 is a schematic enlarged view of a lens protector in accordance with some embodiments of the prior art invention described in U.S. Pat. No. 7,104,657.
Figure 3:
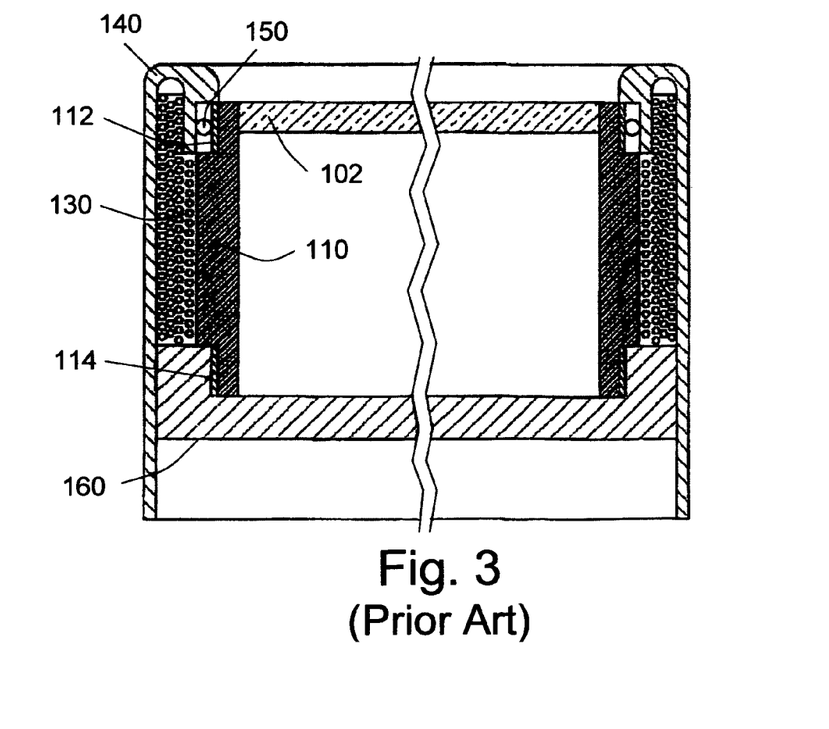
FIG. 3 is a schematic view of a cross-section through a disc-rotor, two of its magnets and its housing-stator, in accordance with some embodiments of the prior art invention described in U.S. Pat. No. 7,104,657.

FIG. 1, FIG. 2, and FIG. 3 show the main features of exemplary embodiments of the invention described in U.S. Pat. No. 7,104,657. FIG. 1 is an oblique schematic view of the inserted end of an endoscope 90, with its distal end covered by a centrifugal lens protector 100. (Note that in the figure the distance between lens protector 100 and the distal end of endoscope 90 is exaggerated for clarity.)

At the distal end of endoscope 90 is a lens 92, held in a housing 96. Optionally one or more channels (not shown in the figures) pass through the interior of endoscope 90 from the proximal end of endoscope 90 to its distal end. These channels are used for a variety of functions, for example, for pumping gas into the volume to be viewed, to suck fluids and particles out from the volume, to spray water for example to clean an area to be viewed or to clean endoscope lens 92, to provide light, to provide therapeutic materials and/or to provide tools. The sizes and number of channels varies between endoscopes, depending on the procedure to be carried out.

Lens protector 100 is affixed at the front of endoscope 90. A disc 102 (or a curved plate or a lens or a filter) covers endoscope lens 92, and optional tube extensions 170 fit into the ends 98 of the channels, continuing the channels through lens protector housing 140. Different embodiments of lens protector 100 may be provided for different sized and configured endoscopes.

Lens protector 100 comprises a short sleeve (not shown in FIG. 1 to FIG. 3) at its proximal end that is used to mount lens protector 100 on the end of endoscope 90, for example, by means of pressure e.g., a sleeve made of elastic material or using a tension band, or an adhesive. Optionally, the short sleeve includes a tear string for fast removal from the endoscope. Alternatively, for some embodiments of endoscope, protector 100 attaches to existing mounting locations on the distal end of the endoscope.

In an alternative embodiment, protector 100 comprises a sheath 190 that encloses endoscope 90. Sheath 190 may be integral with lens protector 100 or it may by attached to the protector after manufacture, for example, it can be fit over the protector when mounting the protector on the endoscope.

A control box 104 controls the activities of lens protector 100 via one or more leads 132 that extend from lens protector 100 to lens protector control box 104. Electrical leads 132 may pass through endoscope 90. Alternatively, leads 132 are embedded in the sheath or lie between the sheath and endoscope 90. Control box 104 comprises an on/off/restart switch 106 and a power supply 108 which may be internal or external to control box 104. Control box 104 optionally includes a band or an adhesive backing for attachment to a handle (not shown in FIG. 1 to FIG. 3) of endoscope 90. The components of control box 104 for the lens protector 100 can be incorporated into the handle or endoscopy suite of the endoscope 90 or can be packaged in a separate unit as is shown in FIG. 1.

FIG. 2 is an oblique schematic view of centrifugal lens protector 100, in accordance with some embodiments of the invention described in U.S. Pat. No. 7,104,657. A substantially transparent disc 102 is provided, which is held in housing 140 in such a way as to enable disc 102 to rotate freely, as described, for example, below. Housing 140 attaches to the distal end of endoscope 90.

Housing 140 is optionally provided with a plurality of extensions 170, which are extensions of the channels in endoscope 90. Some of these channels may be used for suction, to remove fluids or particles from the immediate environment of disc 102. In some embodiments of the invention, housing 140 is provided with depressions or cavities 180 which act as receptacles or attachment points for instruments. In some embodiments some cavities 180 may be located inside extensions 170. One or more of extensions 170 may be used for control wires connecting to instruments outside the endoscope, for example instruments held in cavities 180. Optionally, some channels in the endoscope are used for more than one function.

FIG. 3 is a cross-sectional view of FIG. 2. Disc 102 is provided with a plurality of axially aligned magnets 110. One end of each magnet is affixed to disc 102, for example using an adhesive or using a tension ring surrounding the magnets. Optionally, the magnets are mounted directly on disc 102, for example, being held in depressions formed in disc 102. Magnets 110 extend axially from disc 102 into the interior volume of housing 140. Disc 102 is optionally held in place by a plurality of ball or cylinder bearings 150, which enable rotation. In some embodiments the diameter of a bearing 150 is 0.2 millimeter. Alternatively or additionally, a slip-ring bearing is used. At the base of protector 100, a second bearing 160 is optionally provided, for example, a slip-ring bearing.

In an exemplary embodiment, magnets 110 are interconnected by a pair of optional sliding rings 112 and 114 which serve, as tension rings, to prevent the centrifugal force of rotation from detaching the magnets from disc 102 or causing undue distortion. Sliding rings 112 and 114 slide in contact with bearings 160 and 150. In some embodiments, the life time of protector 100 is relatively short, so wear of the bearings is not crucial. Such slip rings may be mounted on the moving part (e.g. the disc) or on the static part (e.g., housing 140).

A plurality of coils 130 are provided within the body of housing 140, at or close to the inner surface of housing 140. In some embodiments, coils 130 are fabricated by a process of depositing electroconductive material, e.g. copper or silver or platinum or an electroconductive plastic in a specially formed cavity in housing 140. Many different lithographic methods may be used for fabricating coils 130. Alternatively, the coils are deposited on a rigid or flexible substrate and the substrate is inserted into housing 140. Alternatively or additionally, coils 130 are wound on cores, optionally ferromagnetic cores. Coils 130, on their cores, are inserted into a receptive depression in housing 140.

Additional description of different embodiments of the motor assembly of the lens protector 100, including typical dimensions speeds of rotation, arrangements of the coils, etc. are given in U.S. Pat. No. 7,104,657.

Figure 4A:
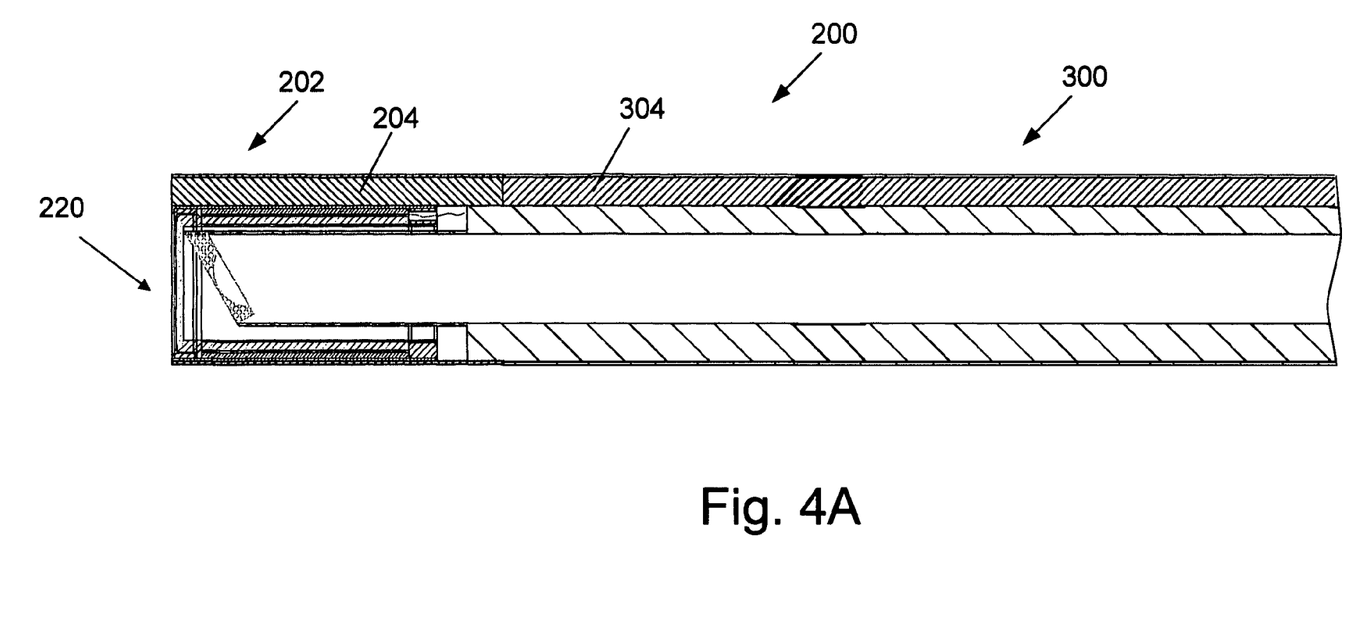
FIG. 4A is a schematic cross-sectional side view of the distal portion of the endoscopic device of the invention.
Figure 4B:
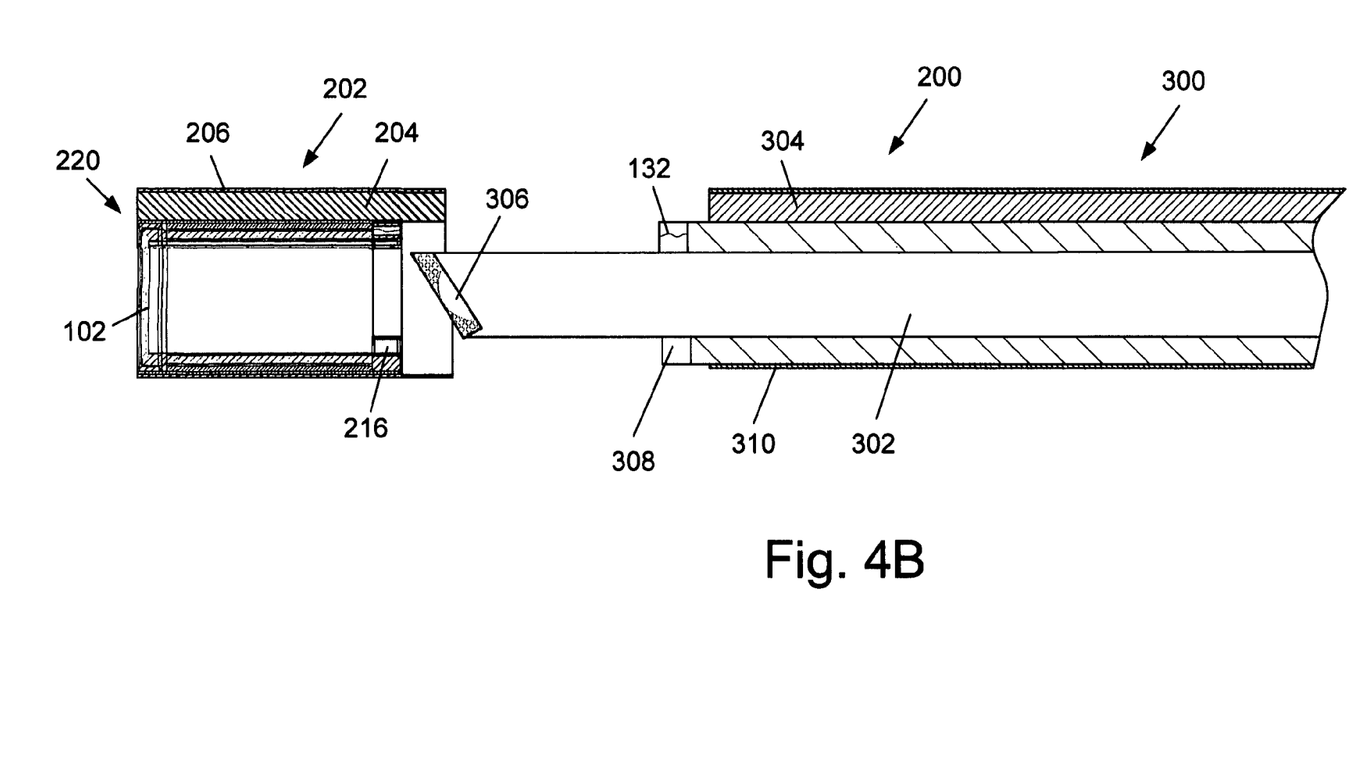
FIG. 4B schematically shows the view of FIG. 4A with the two principle sections of the distal portion of the endoscopic device of the invention separated from each other.

FIG. 4A is a schematic cross-sectional side view of the distal portion 200 of the endoscopic device of the invention. FIG. 4B schematically shows the view of FIG. 4A with the two principle sections of the distal portion 200 of the endoscopic device of the invention axially separated from each other. As is shown in these two figures, the distal portion 200 of the endoscopic device is comprised of an insertion shaft 300 and lens protector unit 202.

Insertion section 300 is similar to the insertion section of conventional endoscopic devices but has been modified as is apparent from the figures and will be described herein below. Insertion section 300 can be rigid, semi-rigid or flexible. Flexible embodiments can comprise cables to bend the distal end or an articulation section to enable reproducible, controlled bending. The main features of insertion section 300 that are of interest regarding the invention are the light carrier 304 and central lumen 302, which contains the optical system that terminates with objective lens 306.

The exact nature of the optical system, which can be any type of system known in the art, e.g. a video camera or an optical fiber bundle or optical relay system to transfer light gathered by objective lens 306 to a proximal image forming system, is not relevant to the present invention and therefore not discussed in detail herein. The light carrier 304 is located adjacent to the outer surface on one side of the interior of insertion section 300. The light carrier conducts light from a light source at the proximal end of the endoscopic device to the distal end of the insertion shaft in order to illuminate the space in front of the objective lens. As in all endoscopic devices a thin elastomeric sheath 310 covers insertion section 300 to prevent the entrance of fluids or other debris into the interior of the device and the passage of light in either direction through the wall of the device.

Unlike conventional endoscopic devices wherein the light carrier terminates on the face of the distal tip in essentially the same plane as the objective lens, the central lumen 302 of insertion shaft 300 of the endoscopic device of the invention comprises a portion that projects distally past the end of light carrier 304 as shown in FIG. 4A and FIG. 4B. The purpose of this unique structure is to allow the decoupling of the light from the optical path when the lens protector unit is attached to the insertion section. Structurally, this is one of the main features that distinguish the present invention from that in U.S. Pat. No. 7,104,657.

The dimensions and shape of the projecting portion of central lumen 302 are determined such that the projecting portion can be inserted into the hollow center of motor assembly 220 of lens protector unit 202 until the objective lens 306, which is attached to the distal end of the projecting portion, is in close proximity to rotatable window 102. Another feature of the present invention is that the distal end of the central lumen 302 of insertion shaft 300 can be configured to hold lens 306 either in a plane perpendicular to the longitudinal axis of the endoscope or at an angle as shown in FIG. 4A and FIG. 4B in order to provide a viewing angle that is optimal for a specific application.

Figure 5:
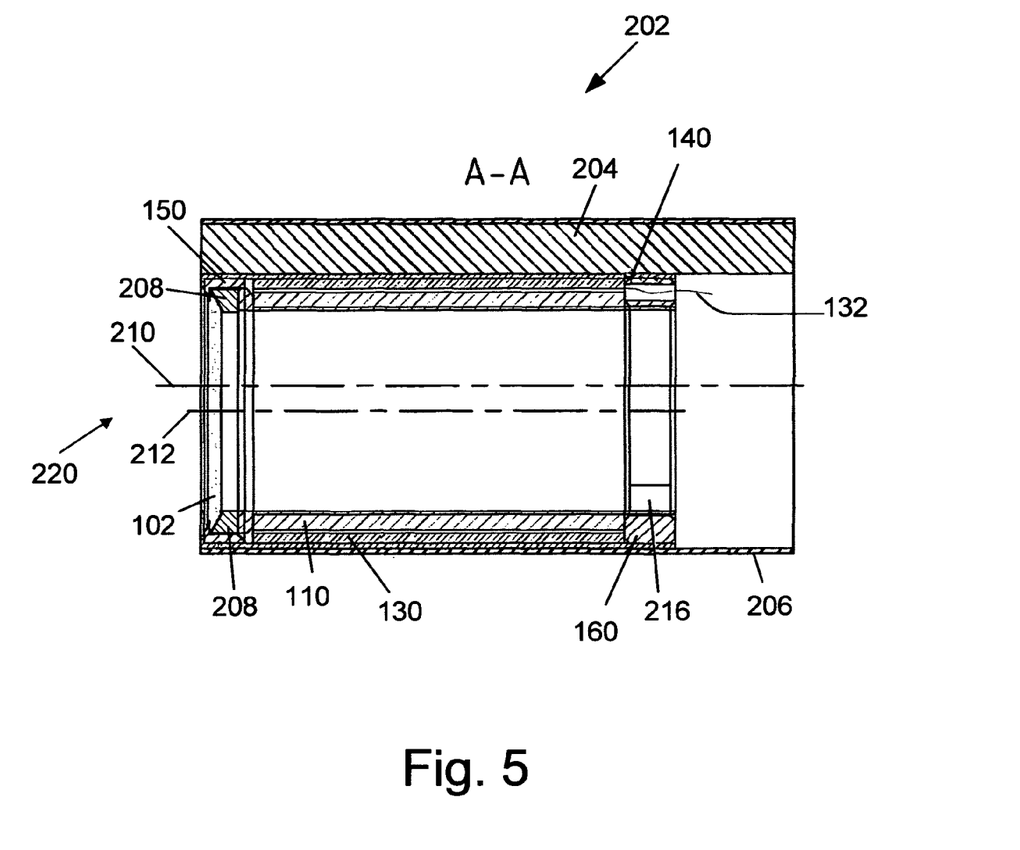
FIG. 5 is a cross-sectional side view of the lens protector unit of the invention.

The lens protector unit 202, which is shown in more detail in cross-sectional side view in FIG. 5, comprises a motor assembly 220, a rotatable transparent window 102 attached to the distal end of the motor assembly, and a light carrier 204 located adjacent to the outer surface on one side of the interior of the lens protector unit. Lens protector unit 202 is surrounded by an outer casing 206.

Figure 6:
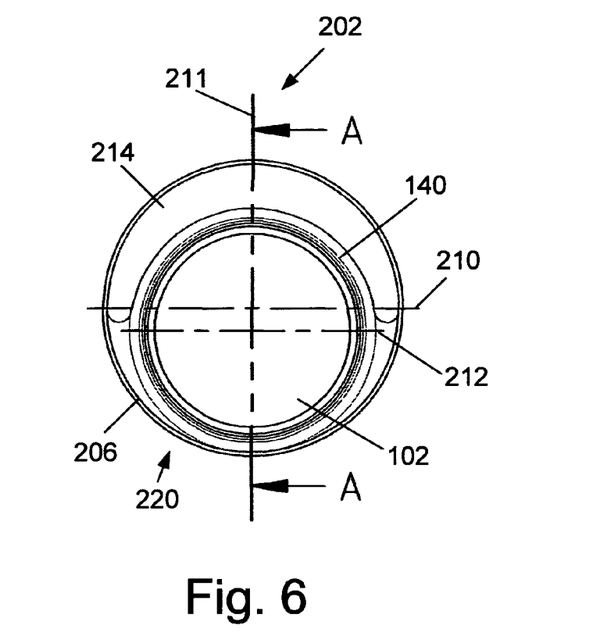
FIG. 6 is a front view of an embodiment of the lens protector unit of the invention.
Figure 7:
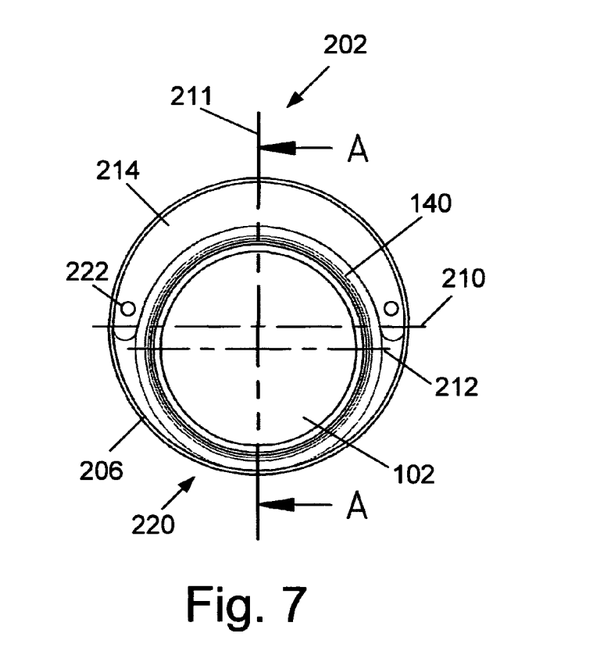
FIG. 7 is a front view of another embodiment of the lens protector unit of the invention that comprises working channels.

Motor assembly 220 is essentially identical mutatis mutandis with centrifugal lens protector 100 described herein above and shown in FIG. 1 to FIG. 3 and described in more detail in U.S. Pat. No. 7,104,657. Referring to FIG. 5, motor assembly 220 comprises housing 140, magnets 110, coils 130, and upper and lower bearings 150 and 160. A window 102 is fixedly attached to extensions 208 of the magnets 110. Window 102 is made of a material that has high optical transmission in the spectral region to which the optical system is sensitive, e.g. glass in the visible region and sapphire in the near infrared. The window 102 rotates with magnets 110 when the coils are activated and the centrifugal force created by the rotation keeps it clear of debris. In FIG. 5, FIG. 6, and FIG. 7 numeral 211 and numeral 210 designate the vertical and horizontal symmetry axes of the lens protector unit 202 respectively. Numeral 212 designates the horizontal symmetry axis of motor assembly 220.

In an embodiment of the invention coils 130 comprise three separate coils each of which is connected via electrical leads 132 to a different phase of a DC power supply 108 (See FIG. 1). The electric circuit for motor assembly 220, which is located control box 104, is adapted such that voltage is applied to only two of the coils at one time. The rotation of the magnetic field relative to the third coil generates a back electromagnetic force (EMF) in it. This back EMF is sensed by the circuitry and, when the EMF reaches a predetermined magnitude, the circuitry switches the DC voltage to another pair of coils. The use of the back EMF switching insures stable rotation of window 102 and enables the motor assembly to be produced at minimum cost since the motor doesn't require brushes.

In addition to the three-phase power supplied to the coils 130 of motor assembly 220 to cause rotation of window 102, an additional current can be supplied from the circuitry in control box 104 to heat the window. The heating current can be supplied either as an AC current to coils 130 or as either an AC or DC current to a separate coil provided for this purpose. Preferably a temperature sensor is provided near window 102 to provide feedback to the circuitry which will supply the heating current at a rate which maintains the temperature in the vicinity of window 102 at a predetermined temperature, ideally 37° C. to prevent condensation on the window.

Light carrier 204 is a fiber optic bundle or other type of light guide used to convey the light from the distal end of light carrier 304 of the insertion shaft 300 to the distal end of the lens protector unit 202.

FIG. 6 is a front view of the lens protector unit 202 of the endoscope 200 of the invention. Vertical symmetry axis 211 also defines plane A-A, the plane of FIG. 5. As a result of the fact that horizontal symmetry axis 212 of motor assembly 220 is lower than horizontal symmetry axis 210 of lens protector unit 202, there is created a roughly crescent shaped area 214 on the distal face of lens protector unit 202, i.e. on the distal face of endoscope 200, that is not covered by rotating window 102. As can be seen from, for example FIG. 6, all or part of area 214 can be utilized to allow the light from light carrier 204 to be projected outwards to illuminate the space in front of window 102. Thus the optical path and the path of the illumination light have been separated and the problem that sometimes occurs with use of the lens protector 100 described in U.S. Pat. No. 7,104,657, i.e. back reflection of light emitted from the endoscope onto the objective lens 309, has been overcome.

Light carrier 204 can be shaped to have a cross-section that coincides with all or part of area 214. If only part of area 214 is used for the illumination, then the remaining part can comprise one or more working channels that can be used for any of the variety of uses known in the art, e.g. insufflation, suction, or introduction of diagnostic or surgical tools. FIG. 7 is a front view of an embodiment of the lens protector unit 202 of the endoscope 200 of the invention that comprises two working channels 222.

As shown in FIG. 4A and FIG. 4B, insertion shaft 300 and lens protector unit 202 are provided as separate units that are joined together to form a single endoscopic device 200. Insertion shaft 300 and lens protector unit 202 can be joined together in several ways known to persons of the art. For example, the distal extension of central lumen 302 and the hollow center of motor assembly 220 can be manufactured such that the former slides very snugly into the latter. As another or additional example, spacer ring 216 in lens protector unit 202 can comprise one or more spring loaded pins that project in the proximal direction and snap into or out of matching bores created in the distal end 308 of the main body of insertion shaft 300. Additionally, an optical coupler (not shown in the figures) of a type known in the art is provided to minimize loss of light at the interface between light carriers 304 and 204 and electrical connectors, e.g. bayonet connectors, are present on distal end 308 and the proximal end of motor assembly 220 to provided electrical continuity of the electrical leads 132 to the motor. These elements can also serve to join insertion shaft 300 and lens protector unit 202 together.

After the distal extension of central lumen 302 is slid into the hollow center of motor assembly 220 a tight fitting elastomeric sleeve can by pulled over the outside of both of them to hold them together. The sleeve can be provided with a tear string that can be used to easily remove it after the procedure allowing the insertion shaft 300 and the lens protector unit 202 to be easily separated.

The inventor wishes to emphasize that, although the word endoscope is commonly associated with medical applications the invention is not meant to be limited to use with medical instruments only. There is a wide range of applications not related to medical procedures in which endoscopic devices (referred to as borescopes in industrial applications) are used and in which the device of the invention can be utilized to allow clearer viewing and protection to delicate optical systems in dirty environments. Examples of such applications are inspection of the interior of motors and engines, inspection of the interior of metal or plastic castings, inspection of hollow spaces in walls, floors, and ceilings of buildings, etc.

In the case of medical applications, after the endoscope 200 is used to carry out a diagnostic, therapeutic, or surgical procedure the lens protector unit 202 can be detached from the insertion shaft 300. In embodiments of the invention insertion shaft 300 is sterilizable and used over and over again in successive procedures and lens protector unit 202 is discarded after each procedure.

Not shown in the figures and not relevant to the invention is the proximal end of endoscope 200. A handle at the proximal end comprises the usual features associated with endoscopic devices, e.g. control levers for the bending/steering cables, entry ports connected to the working channels, and connectors to the endoscopy suite that comprises the illumination source, suction, water, air, and electricity supplies. The handle is also comprises connections to the viewing system and to the control box 104 and power supply 108 for the motor assembly 220.

As in the prior art, the components of the control circuit and power supply for the motor assembly can be provided as separate units or all or some of the components can be incorporated within the endoscopy suite to which the endoscope is connected or within the body or handle of the endoscope.

Although embodiments of the invention have been described by way of illustration, it will be understood that the invention may be carried out with many variations, modifications, and adaptations, without exceeding the scope of the claims.

The invention claimed is:

1. An endoscopic device comprising a distal portion comprised of an insertion shaft and a lens protector unit:
   a. said insertion shaft comprising:
      i. a first light carrier located adjacent to an outer surface on one side of an interior of said insertion shaft;
      ii. a central lumen comprising a portion that projects distally past an end of said first light carrier; and
      iii. an objective lens attached to said distal end of said central lumen; and
   b. said lens protector unit comprising:
      i. a motor assembly comprising a housing, magnets, coils, an upper bearing, and a lower bearing;
      ii. a rotatable transparent window attached to a distal end of said motor assembly, said window having a diameter no greater than that of said housing;
      iii. a second light carrier located adjacent to the outer surface on one side of the interior of said lens protector unit, said second light carrier adapted to convey light from a proximal end of said lens protector unit to a location on a portion of a distal end of said lens protector unit not covered by said rotatable transparent window; and
      iv. an outer casing that encloses said motor assembly and said second light carrier of said lens protector unit such that said second light carrier is located in a space having a roughly crescent shaped cross section between said outer casing and said housing, wherein
said portion of said central lumen that projects distally past the end of said first light carrier has dimensions and shape adapted to allow said projecting portion to be inserted into a hollow center of said motor assembly until said objective lens is in close proximity to said rotatable transparent window; and
a proximal end of said second light carrier in said lens protector unit is optically coupled to a distal end of said first light carrier of said insertion shaft by means of an optical coupler located at said first location.

2. The endoscopic device of claim 1, wherein the rotatable transparent window is integral with a rotor of a motor of the motor assembly.

3. The endoscopic device of claim 1, wherein the housing is integral with a stator of a motor of the motor assembly.

4. The endoscopic device of claim 3, wherein the stator comprises three separate coils each of which is connected via electrical leads to a different phase of a DC power supply.

5. The endoscopic device of claim 4, comprising an electric circuit adapted to activate the motor using back electromagnetic force (EMF) switching.

6. The endoscopic device of claim 3, wherein the heating current is supplied as an AC current to coils of the stator.

7. The endoscopic device of claim 1, wherein a motor of the motor assembly is a magnetic motor.

8. The endoscopic device of claim 7, wherein the motor comprises a plurality of axially disposed magnets, attached to the rotatable transparent window.

9. The endoscopic device of claim 1, comprising an electric circuit adapted to supply current to heat the rotatable transparent window.

10. The endoscopic device of claim 9, wherein the heating current is supplied as either an AC or a DC current to a separate coil adapted to heat the rotatable transparent window.

11. The endoscopic device of claim 9, comprising a temperature sensor near the rotatable transparent window to provide feedback to the circuitry which supplies the heating current in order to supply said current at a rate which maintains the temperature in the vicinity of said rotatable transparent window at a predetermined temperature.

12. The endoscopic device of claim 11, wherein the predetermined temperature is 37.degree.C.

13. The endoscopic device of claim 1, comprising one or more working channels that pass through said endoscopic device from a proximal end of said endoscopic device to a distal end of said lens protector unit.

14. The endoscopic device of claim 1, wherein the insertion shaft is adapted to enable it to be sterilized.

15. The endoscopic device of claim 1, wherein the lens protector unit is adapted to enable it to be discarded after a single use.

* * * * *